(12) United States Patent
Weinberg et al.

(10) Patent No.: US 12,066,624 B2
(45) Date of Patent: Aug. 20, 2024

(54) EYE TRACKING DEVICE AND METHOD THEREOF

(71) Applicant: EYEWAY VISION LTD., Or Yehuda (IL)

(72) Inventors: Yakov Weinberg, Modi'in (IL); Alexandr Logvinenko, Petah Tiqva (IL); Jacob Kagan, Jerusalem (IL); Uri Korogodsky, Ramat Gan (IL); Albert Kashchenevsky, Tel Aviv (IL); Elad Eizner, Ramat Gan (IL); Boris Greenberg, Tel Aviv (IL)

(73) Assignee: EYEWAY VISION LTD., Or Yehuda (IL)

( * ) Notice: Subject to any disclaimer, the term of this patent is extended or adjusted under 35 U.S.C. 154(b) by 0 days.

(21) Appl. No.: 17/758,445

(22) PCT Filed: Jan. 6, 2021

(86) PCT No.: PCT/IL2021/050022
§ 371 (c)(1),
(2) Date: Jul. 6, 2022

(87) PCT Pub. No.: WO2021/140512
PCT Pub. Date: Jul. 15, 2021

(65) Prior Publication Data
US 2023/0045580 A1 Feb. 9, 2023

Related U.S. Application Data

(63) Continuation of application No. 16/742,278, filed on Jan. 14, 2020, now Pat. No. 11,054,639.
(Continued)

(51) Int. Cl.
*G02B 27/00* (2006.01)
*G02B 26/10* (2006.01)
(Continued)

(52) U.S. Cl.
CPC ....... *G02B 27/0093* (2013.01); *G02B 26/101* (2013.01); *G02B 27/017* (2013.01);
(Continued)

(58) Field of Classification Search
CPC ....... G06F 3/013; G02C 11/10; G02B 27/104; G02B 27/0172; G02B 27/017; G02B 26/101; G02B 27/0093
See application file for complete search history.

(56) References Cited

U.S. PATENT DOCUMENTS 785,575 A 3/1905 Ryon
5,596,339 A 1/1997 Furness, III et al.
(Continued)

FOREIGN PATENT DOCUMENTS

CN 1183848 A 6/1998
CN 1770063 A 5/2006
(Continued)

OTHER PUBLICATIONS

Israeli patent application No. 24530; filed Jan. 29, 2019.
(Continued)

*Primary Examiner* — Abbas I Abdulselam
(74) *Attorney, Agent, or Firm* — Kenealy Vaidya LLP

(57) ABSTRACT

The present invention relates to a stereo eye tracking technique. The eye tracking device comprises a processing unit configured and operable for receiving at least one image being indicative of a user's eye; identifying in the image a first data being indicative of pupil's parameters; receiving a second data being indicative of an alternative eye tracking, wherein the second data is more accurate than the first data; and correlating between the first and second data and determining a three-dimensional position and gaze direction of the user's eye.

23 Claims, 9 Drawing Sheets

Related U.S. Application Data

(60) Provisional application No. 62/957,347, filed on Jan. 6, 2020.

(51) Int. Cl.

| | | |
|---|---|---|
| *G02B 27/01* | (2006.01) | |
| *G02B 27/10* | (2006.01) | |
| *G02C 11/00* | (2006.01) | |
| *G06F 3/01* | (2006.01) | |
| *A61B 3/113* | (2006.01) | |
| *G02B 5/20* | (2006.01) | |

(52) U.S. Cl.
CPC ....... *G02B 27/0172* (2013.01); *G02B 27/104* (2013.01); *G02C 11/10* (2013.01); *G06F 3/013* (2013.01); *A61B 3/113* (2013.01); *G02B 5/20* (2013.01); *G02B 2027/0138* (2013.01); *G02B 2027/0178* (2013.01)

(56) References Cited

U.S. PATENT DOCUMENTS

| | | | |
|---|---|---|---|
| 6,657,628 | B1 | 12/2003 | Cook |
| 6,943,754 | B2 | 9/2005 | Aughey et al. |
| 7,331,929 | B2 | 2/2008 | Morita et al. |
| 7,470,025 | B2 | 12/2008 | Iwanaga |
| 7,542,210 | B2 | 6/2009 | Chirieleison, Sr. |
| 7,637,615 | B2 | 12/2009 | Yamada |
| 7,936,519 | B2 | 5/2011 | Mukawa et al. |
| 8,289,231 | B2 | 10/2012 | Budd et al. |
| 8,384,999 | B1 | 2/2013 | Crosby et al. |
| 9,256,069 | B2 | 2/2016 | Wada |
| 9,265,415 | B1 | 2/2016 | Starner et al. |
| 10,042,161 | B2 | 8/2018 | Greenberg |
| 10,539,789 | B2 | 1/2020 | Greenberg |
| 11,054,639 | B2 | 7/2021 | Greenberg |
| 2001/0035938 | A1 | 11/2001 | Lai et al. |
| 2004/0109135 | A1 | 6/2004 | Watanabe et al. |
| 2007/0159599 | A1 | 7/2007 | Yamada |
| 2008/0151185 | A1 | 6/2008 | Saito et al. |
| 2009/0122385 | A1 | 5/2009 | Hilton |
| 2010/0045571 | A1 | 2/2010 | Yamamoto |
| 2011/0213664 | A1 | 9/2011 | Osterhout et al. |
| 2012/0154277 | A1 | 6/2012 | Bar-Zeev et al. |
| 2013/0016413 | A1 | 1/2013 | Saeedi et al. |
| 2013/0021226 | A1 | 1/2013 | Bell |
| 2013/0044042 | A1 | 2/2013 | Olsson et al. |
| 2013/0120712 | A1 | 5/2013 | Spasovski |
| 2014/0108842 | A1* | 4/2014 | Frank ............... G06F 1/3212 713/323 |
| 2014/0180162 | A1 | 6/2014 | Schuhrke et al. |
| 2015/0009117 | A1* | 1/2015 | Peters ............... G06F 3/013 345/156 |
| 2015/0199006 | A1* | 7/2015 | He ................... A61B 3/0041 345/158 |
| 2016/0302663 | A1* | 10/2016 | Fayolle ............. G02B 5/1866 |
| 2019/0005679 | A1 | 1/2019 | Nie |
| 2021/0157133 | A1* | 5/2021 | De Bougrenet ........ G06F 3/011 |
| 2021/0173474 | A1* | 6/2021 | Sztuk ............... G06T 19/006 |

FOREIGN PATENT DOCUMENTS

| | | |
|---|---|---|
| CN | 1810202 A | 8/2006 |
| CN | 101107557 | 1/2008 |
| CN | 101583898 | 11/2009 |
| CN | 102447931 A | 5/2012 |
| CN | 102906623 | 1/2013 |
| JP | H10319342 | 12/1998 |
| JP | 2001216530 | 8/2001 |
| JP | 2004191962 | 7/2004 |
| JP | 2005505787 A | 2/2005 |
| JP | 2006058505 A | 3/2006 |
| JP | 2008067218 A | 3/2008 |
| JP | 2008145701 A | 6/2008 |
| JP | 2008529054 | 7/2008 |
| JP | 2010091944 | 4/2010 |
| JP | 2010139575 | 6/2010 |
| JP | 2010175829 | 8/2010 |
| JP | 2013210587 | 10/2013 |
| WO | 9418883 A1 | 9/1994 |
| WO | 0079327 A1 | 12/2000 |
| WO | 2006019028 A1 | 2/2006 |
| WO | 2006078177 | 7/2006 |
| WO | 2009094643 | 7/2009 |
| WO | 2010054473 | 5/2010 |
| WO | 2011106798 | 9/2011 |
| WO | 2012082807 | 6/2012 |
| WO | 2013117999 | 8/2013 |
| WO | 2013163468 | 10/2013 |
| WO | 2014030158 | 2/2014 |
| WO | 2014031326 | 2/2014 |

OTHER PUBLICATIONS

Barsingerhorn AD, Boonstra FN, Goossens HH. Optics of the human cornea influence the accuracy of stereo eye-tracking methods: a simulation study. Biomed Opt Express. 2017; 8(2):712-725. Published Jan. 9, 2017. doi:10.1364/BOE.8.000712.

Ignace Hooge, Kenneth Holmqvist, Marcus Nyström, "The pupil is faster than the corneal reflection (CR): Are video based pupil-CR eye trackers suitable for studying detailed dynamics of eye movements?", Vision Research, vol. 128, 2016, pp. 6-18, ISSN 0042-6989, doi: 10.1016/j.visres.2016.09.002.

Constable P.A, et al, International Society for Clinical Electrophysiology of Vision. ISCEV Standard for clinical electro-oculography (2017 update). Doc Ophthalmol. 2017;134(1):1-9.

McCamy et al: Simultaneous recordings of ocular microtremor and microsaccades with a piezoelectric sensor and a video-oculography system. Peer J. 1. e14. 10.7717/peerj. 14. (Feb. 12, 2013).

Kohlbecher S., et al. "Calibration-free eye tracking by reconstruction of the pupil ellipse in 3D space", Proceedings of the 2008 Symposium on Eye Tracking Research & Applications: 135-138, Mar. 26, 2008.

Wood E., et al. "EyeTab: model-based gaze estimation on unmodified tablet computers", Proceedings of the 2014 Symposium on Eye Tracking Research & Applications: 207-210, 2014.

\* cited by examiner

EYE TRACKING DEVICE AND METHOD THEREOF

TECHNOLOGICAL FIELD

The present invention relates to the field of eye tracking in general and in particular to a pupil tracking device and a method thereof.

BACKGROUND ART

References considered to be relevant as background to the presently disclosed subject matter are listed below:
[1] Barsingerhorn AD, Boonstra FN, Goossens HH. Optics of the human cornea influence the accuracy of stereo eye-tracking methods: a simulation study. Biomed Opt Express. 2017; 8(2):712-725. Published 2017 Jan. 9. doi:10.1364/BOE.8.000712
[2] Ignace Hooge, Kenneth Holmqvist, Marcus Nystrom, "The pupil is faster than the corneal reflection (CR): Are video based pupil-CR eye trackers suitable for studying detailed dynamics of eye movements?", Vision Research, Volume 128, 2016, Pages 6-18, ISSN 0042-6989, doi: 10.1016/j.visres.2016.09.002.

Acknowledgement of the above references herein is not to be inferred as meaning that these are in any way relevant to the patentability of the presently disclosed subject matter.

BACKGROUND

Using eye viewing cameras (usually IR), among all visible eye features, the pupil is the feature that can be recognized in the most reliable and precise way. In other words, the pupil is the best recognizable feature in eye images from cameras, both in visible and near IR spectra. It is the darkest part of the eye and possesses very sharp and distinctive borders. For this reason, all current video-based eye tracking algorithms include pupil recognition. However, a fundamental drawback of pupil-based eye tracking lies in the fact that the pupil, residing behind the cornea, undergoes large distortions which are hard to account for due to large variations in cornea shape in each person, as well as substantial variations in the pupil size due to dilation [1]. Therefore, the main limitation of pupil-based eye tracking is that pupil visual appearance is strongly distorted by the cornea. The shape of the cornea can vary greatly from person to person, and the fact that pupil dilates substantially and its size is unknown, makes it extremely difficult to understand the direction of eye gaze and other parameters of eye location, based merely on information on the pupil, even if more than one camera is used to observe the pupil.

The most popular video-based eye tracking approach used today tracks relative position of the pupil with LED flaring on the cornea. This requires heavy calibration that involves the user following the visual target in a known (or in tracked, with forward facing cameras) location, and estimating which gaze direction corresponds to which pupil/LED flares' visual appearance. Moreover, this approach suffers from inherent accuracy problems since it is susceptible to user's calibration errors (i.e. user did not follow the target precisely during the complex and long calibration procedure). Furthermore, tracker slippage relative to the user's head makes the calibration data for initial relative position, not accurate. The drawbacks mentioned above, limit the accuracy of estimations of the eye position parameters (e.g. gaze direction [2]). Some work has been done in the direction of deducing the cornea shape from LED flares and underlying features distortion, as well as adding more cameras. None of these works produced stable and reliable results.

GENERAL DESCRIPTION

Eye tracking refers to the process of tracking movements of the eye and determining where the user is looking (i.e. gaze direction). The different techniques described above, estimate approximately the scale of eye movements, and may indicate that a movement has occurred. However, they do not measure six degrees of freedom of eye movement. Moreover, these systems do not track the visual features of the eye. One of the problems associated with tracking the visual features of the eye, is that the most distinctive features of the eye are located on the iris. Both pupil and iris are strongly distorted by the corneal lens. The shape of this lens differs from person to person, so it presents a challenge to understand where exactly these features are located. Astigmatism (cornea asymmetry) further complicates this issue. The limbus (i.e. the border between the white sclera and darker iris) is not distorted by the cornea, but it looks very uniform, is slightly blurred, and does not have any prominent features sought by classical image processing algorithms. The technique of the present invention enables to assess static and dynamic properties of an eye, such as eye position, gaze direction, diameter, shape of the pupil, etc. The present invention is based on a stereo pupil tracking with at least one camera referred as a "pupil tracker", together with another input for eye tracking, referred to as an "alternative eye tracker" or "accurate tracker". This other input may be more accurate (but potentially noisier) than the one received from the data, which is received from the camera, this being "pure pupil-based eye tracking". It should be noted that although, as described above, pupil tracking accuracy has inevitable limitations, the precision (i.e. low noise) of pupil tracking may be quite high because of its distinctive features and clear borders.

Therefore, according to a broad aspect of the present invention, there is provided an eye tracking device, comprising: a processing unit configured and operable for: receiving at least one image being indicative of a user's eye; identifying in the image a first data being indicative of pupil's parameters; receiving a second data being indicative of an alternative eye tracking, wherein the second data is more accurate than the first data; and correlating between the first and second data and determining a three-dimensional position and gaze direction of the user's eye. The second data may comprise at least one of eye position, gaze direction, parameters of the eye, parts of the eye location, rotation of the eye around optical axis, or eyelids location. The first data may comprise at least one of diameter or shape of the pupil.

In some embodiments, the processing unit is configured to determine the gaze direction based at least in part on at least one of a regression algorithm, a computer vision algorithm, a machine learning regression model, or a neural network. The processing unit may thus be configured and operable to correlate between the first and second data by applying a regression model. Additionally or alternatively, the processing unit may be configured and operable to construct a regression map between the pupil tracking and the alternative eye tracking parameters creating a stereo pupil tracking system. In particular, the regression map may be constructed between the pupil tracking and the at least one limbus tracking parameter. Additionally or alternatively, the processing unit may be configured and operable to receive the alternative eye tracking parameters and to update the regression map accordingly. The regression algorithm may comprise correlating between parameters measured from the pupil tracker to parameters measured with the alternative eye tracker. The set of parameters measured from the alternative eye tracker may be gaze direction, as well as parameters of the eye, or parts of the eye location.

As described above, the parameters of the eye may comprise at least one limbus tracking parameter including at least one of limbus center X, Y and Z, limbus plane pitch or limbus plain yaw. For example, for the alternative eye tracker it may be at least one parameter of the set of five degrees of freedom (5DOF) parameters described for example in Israeli patent application No. 264530 assigned to the same assignee that the present invention and which is incorporated herein by reference. The set of five degrees of freedom (5DOF) parameters comprises limbus center X, Y and Z, limbus plane pitch and limbus plain yaw. In addition it may be other parameters like rotation of the eye around optical axis, eyelids location, limbus radius, etc. Additionally or alternatively, the processing unit may be configured and operable to receive at least one limbus tracking parameter and to update the regression map accordingly.

Constantly measuring the pupil tracking parameters with corresponding eye tracker parameters allows gradual construction of a regression map between the pupil tracking and the eye tracking parameters. The repetitive measurements of the eye tracking parameters, together with eye movement models, allows improving the regression map over time, and eventually receiving accurate and precise eye tracking. This technique may integrate self-learning processing.

Additionally or alternatively, the processing unit may also be configured and operable to perform a data fusion between the first and second data. Additionally or alternatively, the processing unit may be configured and operable to determine a three-dimensional position and gaze direction of the user's eye by extrapolation the first data using the regression model.

According to another broad aspect of the present invention, there is provided a method for eye tracking. The method comprises receiving image data indicative of at least one image of a user's eye; identifying in the image a first data being indicative of pupil's parameters; receiving a second data being indicative of alternative eye tracking, wherein the second data is more accurate than the first data; and correlating between the first and second data to thereby determine a three-dimensional position and gaze direction of the user's eye.

In some embodiments, the method further comprises capturing at least one image of a user's eye. Additionally or alternatively, the method may further comprise applying a regression model to correlate between the first and second data. Additionally or alternatively, the method may further comprise constructing a regression map between the pupil tracking and the alternative eye tracking parameters. Additionally or alternatively, the method may further comprise continuously receiving alternative eye tracking parameters and updating the regression map accordingly. Additionally or alternatively, the method may further comprise performing a data fusion between the first and second data. Additionally or alternatively, the method may further comprise extrapolating the first data using the regression model to determine the three-dimensional position and gaze direction of the user's eye. Additionally or alternatively, the method may further comprise constructing a regression map between the pupil tracking and the limbus tracking parameters. Additionally or alternatively, the method may further comprise receiving at least one limbus tracking parameter and updating the regression map accordingly.

The present invention also provides an improved eye projection system, comprising an eye projection optical module utilizing a gaze tracking deflector. The eye projection system is configured generally similar to the system described in U.S. Pat. No. 10,539,789, assigned to the assignee of the present application, but utilizes the eye projection optical module in which a gaze tracking deflector comprises a field selector optical module including a diffractive structure.

More specifically, the eye projection system comprises: an image projection system, an eye projection optical module, and a gaze tracking controller. The image projection system is adapted to obtain image data and produce an image projection comprising a plurality of light beam portions corresponding to pixels of the image data. The eye projection optical module is adapted to direct the plurality of light beam portions towards an eye of a user. The eye projection optical module comprises: a gaze tracking deflector comprising an addressable optical deflecting unit located along the general optical propagation path; and the field selector optical module comprising the diffractive structure located in the optical path downstream from the addressable optical deflecting unit with respect to a light propagation direction through the system and configured and operable for directing beams of light propagating along various respective optical paths corresponding to different gaze directions towards corresponding locations of the pupil associated with said different gaze directions respectively.

The gaze tracking controller is configured and operable for controlling the operation of at least one of the image projection system and the eye projection optical module in accordance with data indicative of a gaze direction of the eye, so as to direct the plurality of light beam portions of the projected image onto a retina of the eye in accordance with a line of sight of the eye at different gaze directions to thereby compensate for changes in the gaze direction, while not compensating for changes in the line of sight that are associated with at least one of saccadic or tremor eye movements of the eye, thereby providing that the projected image on the retina, in any specific gaze direction, appears stable and fixed to extent permitted by saccadic eye movement.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The technique of the present invention provides at least one of the 5 DOFs of the eye (e.g. pupil feature), given at least one image. As described above, the pupil feature has very sharp and well distinguishable borders, resulting in high SNR, it occupies a small area of the image, thus working with it takes relatively small computations, and it can be well observed in a wide range of gaze directions. However, the position and orientation found in measurements are highly distorted by corneal refraction, changes in ambient illumination cause changes in the pupil size and center position, and people often have irregular pupil forms, rendering adequate pupil description to be complicated.

Figure 1A:
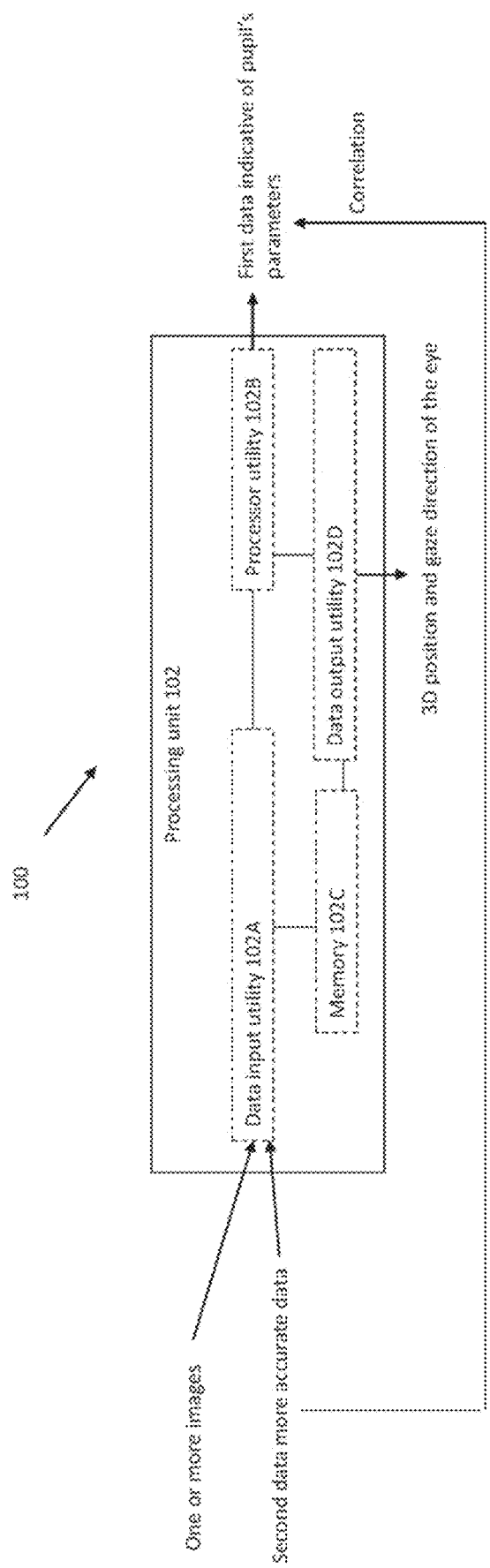
FIG. 1A is a schematic block diagram illustrating, in a non-limiting manner, the eye tracking device for determining a three-dimensional position and gaze direction of the user's eye.

Reference is made to FIG. 1A illustrating an eye tracking device 100 comprising: a processing unit 102 being typically processor-based and including inter alia a memory utility 102C for storage, data input and output utilities (102A and 102D), and a data processor utility 102B. Data input utility 102A is configured and operable for receiving (1) at least one image being indicative of a user's eye and (2) a second data being indicative of an alternative eye tracking, wherein the second data is more accurate than the first data.

Processor utility 102B is configured and operable for identifying in the image a first data being indicative of pupil's parameters (e.g. diameter and/or shape of the pupil), correlating between the first and second data and determining a three-dimensional position and gaze direction of the user's eye. Data input utility 102A may comprise a communication interface being appropriately configured for connecting the processor utility 102B, via wires or wireless signal transmission (e.g. via communication network(s)), to either a measurement device supplying the data (i.e. images and second data) or to an external memory (database) where such data have been previously stored (being supplied to from measurement device(s)). The communication interface may be a separate utility from processor utility 102B or may be integrated within processing unit 102. When the communication interface is a separate unit from processing unit 102, processing unit 102 may comprise a transceiver permitting to be connected to the communication interface and to transmit and/or receive data. When the communication interface is integrated within processing unit 102, it may be included in the data input utility 102A and the data output utility 102D of processing unit 102. The processing unit 102 may comprise a transceiver permitting to be connected to a communication unit and to transmit and/or receive data.

The processing unit 102 may be configured as an electronic module for collecting and processing data. It should be noted that all required operations may be controlled by means of a processing utility, such as a DSP, microcontroller, FPGA, ASIC, etc., or any other conventional and/or dedicated computing unit/system. The term "processing utility" should be expansively construed to cover any kind of electronic device with data processing capabilities, including, by way of non-limiting example, personal computers, servers, computing systems, communication devices, processors (e.g. digital signal processor (DSP), microcontrollers, field programmable gate array (FPGA), application specific integrated circuit (ASIC), etc.) and other electronic computing devices. The processing utility may comprise a general-purpose computer processor, which is programmed in software to carry out the functions described hereinbelow. Also, operations in accordance with the teachings herein may be performed by a computer specially constructed for the desired purposes or by a general-purpose computer specially configured for the desired purpose by a computer program stored in a computer readable storage medium. The different elements of the processing unit (electronic unit and/or mechanical unit) are connected to each other by wires or are wireless. The software may be downloaded to the processing utility in electronic form, over a network, for example, or it may alternatively be provided on tangible media, such as optical, magnetic, or electronic memory media. Alternatively or additionally, some or all of the functions of the processing unit may be implemented in dedicated hardware, such as a custom or semi-custom integrated circuit, or a programmable digital signal processor (DSP). The terms processing unit and processor utility are used herein interchangeably, and furthermore refer to a computer system, state machine, processor, or the like, designed to perform arithmetic or logic operations using logic circuitry that responds to and processes the instructions that drive a computer.

The techniques and system of the present invention can find applicability in a variety of computing or processing environments, such as computer or process-based environments. The techniques may be implemented in a combination of software and hardware. The techniques may be implemented in programs executing on programmable machines such as stationary computers being configured to obtain raw log data, as has also been described above. Program code is applied to the data entered using the input device to perform the techniques described and to generate the output information. The output information can then be applied to one or more output devices.

Each program may be implemented in a high-level procedural or object-oriented programming language to communicate with a processed based system. However, the programs can be implemented in assembly or machine language, if desired.

In other embodiments, the technique of the present invention can be utilized over a network computing system and/or environment. Several computer systems may be coupled together via a network, such as a local area network (LAN), a wide area network (WAN) or the Internet. Each method or technique of the present invention as a whole or a functional step thereof could be thus implemented by a remote network computer or a combination of several. Thus, any functional part of eye tracking device 100 can be provided or connected via a computer network. In addition, the processing unit can also remotely provide processor services over a network.

Each such program may be stored on a storage medium or device, e.g., compact disc read only memory (CD-ROM), hard disk, magnetic diskette, or similar medium or device, that is readable by a general or special purpose programmable machine for configuring and operating the machine when the storage medium or device is read by the computer to perform the procedures described in this document. The eye tracking device may also be implemented as a machine-readable storage medium, configured with a program, where the storage medium so configured causes a machine to operate in a specific and predefined manner.

The present invention uses eye tracking methods that are not affected by the problems of pupil-based tracker mentioned in the previous paragraph. The invention provides a combination of a first data being indicative of pupil measurements and a second data being indicative of "Alternative Eye Tracker" measurements. The second data may comprise the eye position and/or the gaze direction and/or the parameters of the eye and/or the parts of the eye location and/or the rotation of the eye around optical axis and/or the eyelids location This results with the precision of the pupil measurement and the accuracy of the "Alternative Eye Tracker" one. To this end, a correlation between the gaze direction and the "Alternative Eye Tracker" and pupil measurements is provided. The "Alternative Eye Tracker" measurement can be readily related to the gaze direction. The pupil and "Alternative Eye Tracker" measurements are then correlated by using for example a regression model between the two. Both pupil and "Alternative Eye Tracker" data allows to construct a regression between the pupil and "Alternative Eye Tracker" measurements.

Once the regression has been estimated, at least one of the following modes may be used:
 a. When both pupil and "Alternative Eye Tracker" are measured, a data fusion algorithm (e.g., Kalman filter) between the first and second data is performed, resulting in better precision and accuracy in the eye properties estimates.
 b. When only pupil is measured, the regression map may be used to extrapolate the first data and recover the eye properties based only on the pupil measurement.

The pupil may be visible in a wider range of gaze directions, hence using the extrapolated regression allows the device to work in an extended range of gaze directions. Measuring the pupil alone even when both "Alternative Eye Tracker" and pupil have data, reduces the number of computations, resulting in reduced computational time and power consumption.

The regression can be constructed whenever both "Alternative Eye Tracker" and pupil are measured. Therefore, there is a time interval at the beginning of the session when the data is collected to construct the regression. The data acquisition is continued as much as possible, as this increases the sample size, ameliorating the quality of the regression and covers a broader range of eye states. This data may be used also to improve already recorded historic eye tracking data. One of the examples of "Alternative Eye Tracker" is described in the Israeli patent application No. 24530.

Eye tracking systems may track inter alia the limbus (the boundary between sclera and iris regions), or the pupil-iris-boundary, to measure relative eye rotation. It should be noted that the limbus is not influenced by the optical power of the cornea, and therefore tracking the limbus provides accurate results. Moreover, the limbus creates a straight plane. The limbus defines the region of connection between the iris's muscles and therefore there is a direct correlation between the three-dimensional parameters of the limbus and the three-dimensional parameters of the eye. Unfortunately, the limbus is more a transitional zone between the cornea and the sclera, rather than a sharp boundary.

The limbus has some redeeming features: it has somewhat fuzzy borders, it occupies a larger area, and it is harder to observe in a wide range of gaze directions. However, the limbus is located outside the cornea, it is free of corneal optical distortions, its size is independent of the ambient light, and its form is quite regular across the population.

In some embodiments, the invention provides a combination of a first data being indicative of pupil measurements, and a second data being indicative of limbus measurements. This results in precision of the pupil measurement, and accuracy of the limbus measurement. To this end, a correlation between the gaze direction and the limbus and pupil measurements is provided. The limbus measurement, being distortion free, can be readily related to the gaze direction. The pupil and limbus measurements are then correlated by using, for example, a regression model between the two. This regression reflects both individual characteristics of the user's eye, and the position of the cameras with respect to the eye. Both pupil and limbus data are found in the images, to construct a regression between the pupil and limbus measurements.

Once the regression has been estimated, at least one of the following modes may be used:
 c. When both pupil and limbus are measured, a data fusion algorithm (e.g. Kalman filter) is performed, resulting in better precision and accuracy in the eye from 5 DOF estimates.
 d. When only the pupil is measured, the regression may be used to extrapolate and recover the eye, resulting in 5 DOF, based only on the pupil measurement.

The pupil is visible in a wider range of gaze directions, hence using the extrapolated regression allows the device to work in an extended range of gaze directions. Measuring the pupil alone, even when both limbus and pupil are visible, also has advantages, as it reduces the number of computations, resulting in reduced computational time and power consumption.

The regression can be constructed only whenever both limbus and pupil are measured. Therefore, there is a time interval at the beginning of the session when the data is collected to construct the regression. The data acquisition is continued as much as possible, as this increases the sample size, ameliorating the quality of the regression and covering a broader range of eye states. This data may be used also to improve already recorded historic eye tracking data. The regression is dependent on the position of the eye relative to the camera, which can change during the session. This circumstance requires monitoring and detecting changes in head/camera positions and reconstructing the regression map accordingly. The aforementioned circumstances show the need to continuously update the regression map.

Figure 1B:
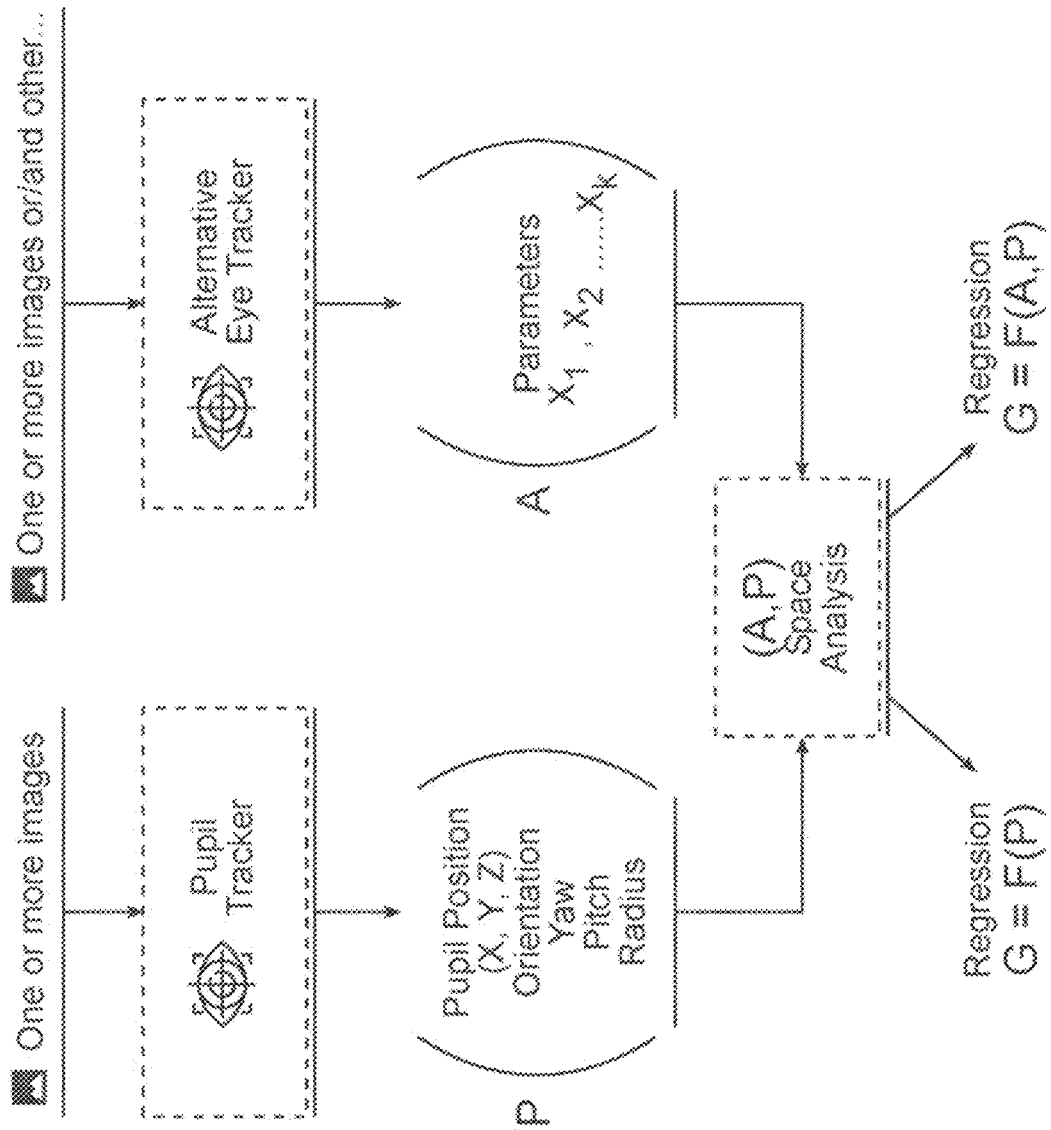
FIGS. 1B-1C are more specific block diagrams illustrating, in a non-limiting manner, possible eye tracking devices according to some embodiments of the present invention.

Reference is made to FIG. 1B, exemplifying a block diagram illustrating the main functional parts of the eye tracking device of the present invention. The eye tracking device comprises a processing unit configured and operable for receiving at least one image being indicative of a user's eye, identifying in the image a first data being indicative of pupil's parameters, receiving a second data being indicative of eye tracking, wherein the second data is more accurate than the first data, correlating between the first and second data and determining a three-dimensional position and gaze direction of the user's eye. To this end, the processing unit may comprise a pupil tracker being configured and operable to receive at least one image being indicative of a user's eye and identify in the image a first data being indicative of pupil's parameters. The pupil's parameters may comprise at least one of pupil position i.e. (x, y, z), orientation (e.g. yaw, pitch) and radius of the pupil. The processing unit may also comprise an accurate tracker being configured and operable to receive a second data being indicative of eye tracking, wherein the second data is more accurate than the first data. The second data may comprise eye parameters such as $X_1$, $X_2 \ldots X_k$. The pupil tracker and the accurate tracker may be separate module or may be the same module performing different functions.

The processing unit is configured and operable to correlate between the first and second data and determining a three-dimensional position and gaze direction of the user's eye. The correlation is represented in the figure as a space analysis (A, P). The regression may be in the form of $G=F(P)$, wherein G is a set of gaze related parameters which need to be measured, F is a regression function, A is the alternative eye tracker parameters, P are the pupil parameters.

In some embodiments, a regression map is created correlating between the second data (i.e. the alternative eye tracking parameters) and the first data (i.e. the pupil tracking). Additionally or alternatively, a regression map is used to determine the first data or the second data.

To create a regression map, a Principal Component Regression (PCR) method may be used. For example, the second data may comprise eye tracker parameters $X_1, X_2 \ldots X_k$ and the first data may comprise pupil tracker parameters x, y, z, nx, ny, nz, and r. These k+7 parameters may be measured and stored at each moment of time generating an history of a k+7-dimensional cloud of measurements. Using the PCR method, a manifold of smaller dimension may be determined and each new measurement vector may be then projected to this manifold. This manifold represents the regression map correlating between the second data and the first data. This process enables reducing a noise level and receiving a cleaner signal.

Figure 1C:
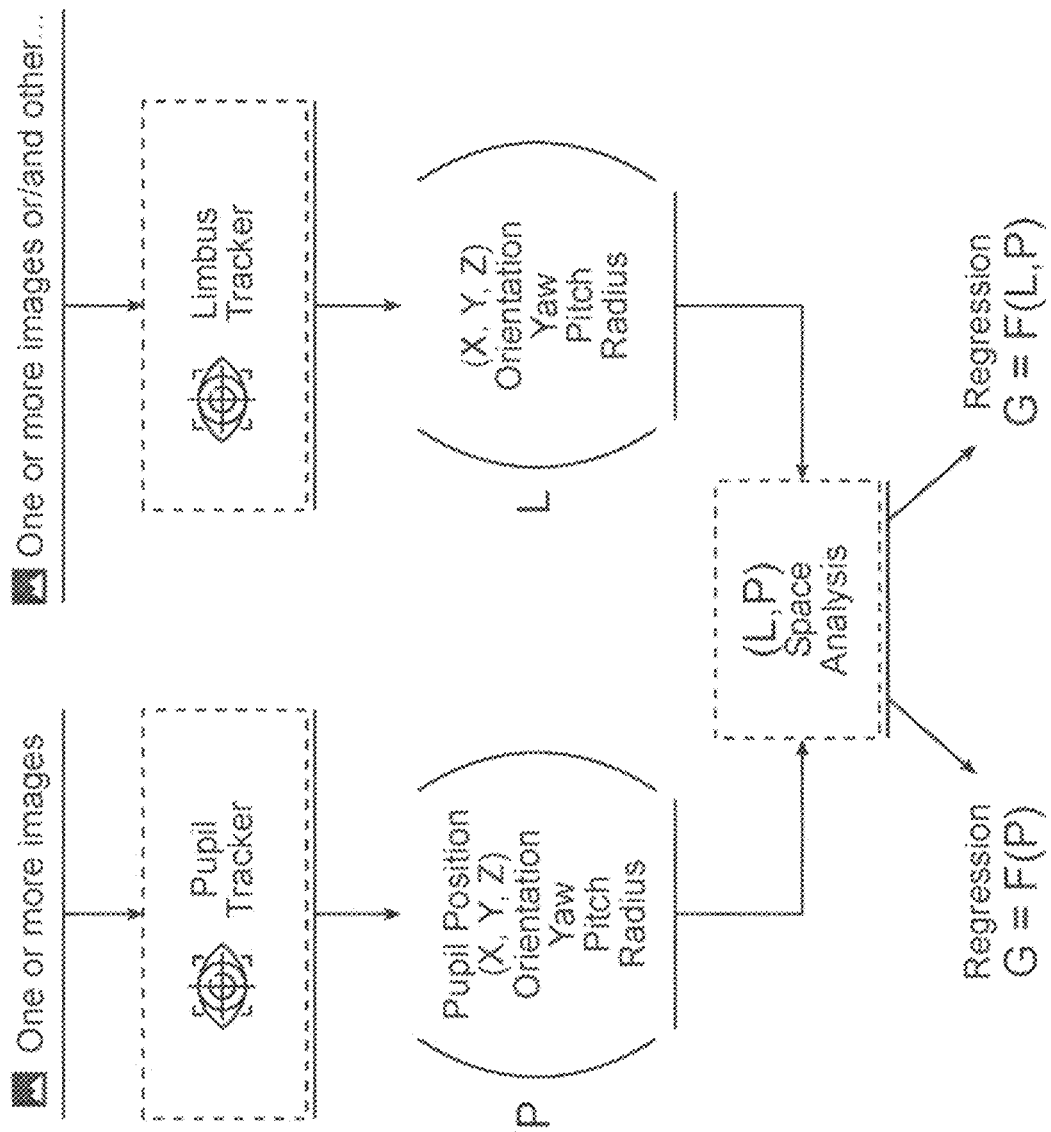

Reference is made to FIG. 1C, exemplifying a block diagram illustrating a specific embodiment in which the second data comprises limbus parameters obtained for example by using the technique described in Israeli patent application No. 264530 assigned to the same assignee that the present invention. The limbus tracking parameter may comprise the limbus center X, Y and Z and/or the limbus plane pitch and/or limbus plain yaw. In this embodiment, the accurate tracker is a limbus tracker providing limbus parameters. The correlation is represented in the figure as a space analysis (L, P). The regression may be in the form of G=F (L, P), wherein G is a set of gaze related parameters which need to be measured, F is a regression function, A is the alternative eye tracker parameters, P are the pupil parameters and L are the limbus tracker parameters.

Figure 2:
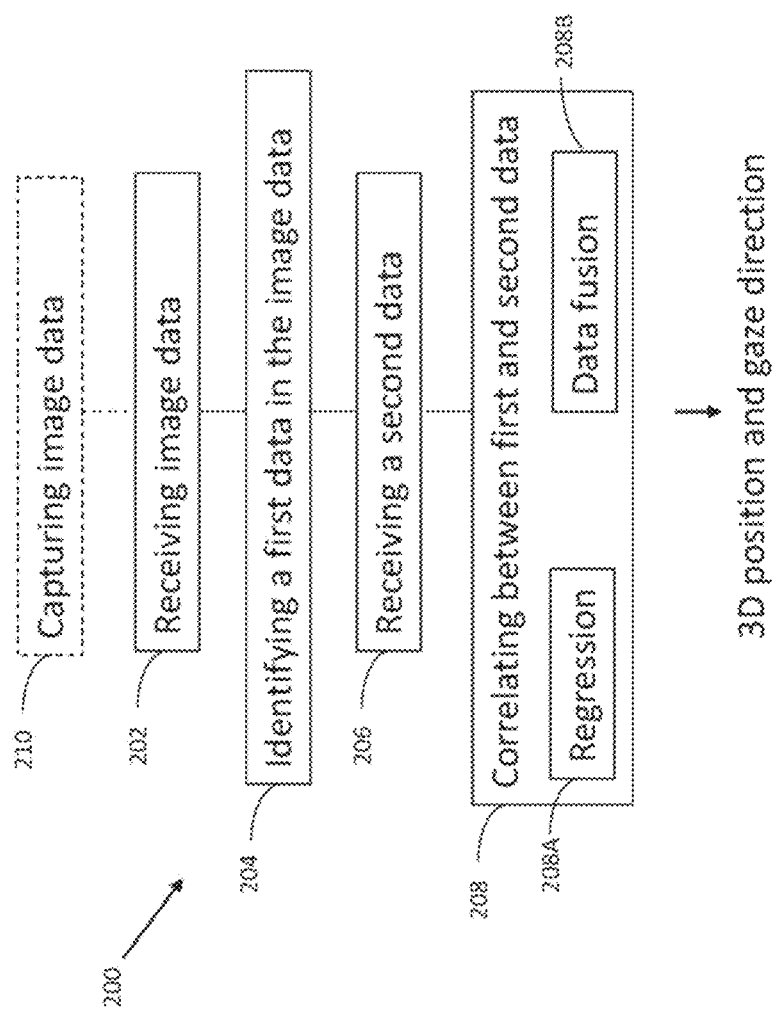
FIG. 2 is a general flow chart illustrating, in a non-limiting manner, a possible method for eye tracking.

Reference is made to FIG. 2, illustrating a method 200 for eye tracking. Method 200 comprises receiving in 202 image data indicative of at least one image of a user's eye, identifying in 204 in the image a first data being indicative of pupil's parameters; receiving in 206 a second data being indicative of alternative eye tracking, wherein the second data is more accurate than the first data; and correlating in 208 between the first and second data to thereby determine a three-dimensional position and gaze direction of the user's eye. To correlate between the first and second data in 208, a regression model 208A may be applied. This may be implemented by constructing a regression map between the pupil tracking and the alternative eye tracking parameters (e.g. the limbus tracking parameters). Alternative eye tracking parameters may be continuously received to update the regression map accordingly. The first data may be then extrapolated using the regression model to determine the three-dimensional position and gaze direction of the user's eye. The regression map between the pupil tracking and the at least one limbus tracking parameter Alternatively or additionally, to correlate between the first and second data in 208, a data fusion may be performed between the first and second data in 208B.

Figure 3A:
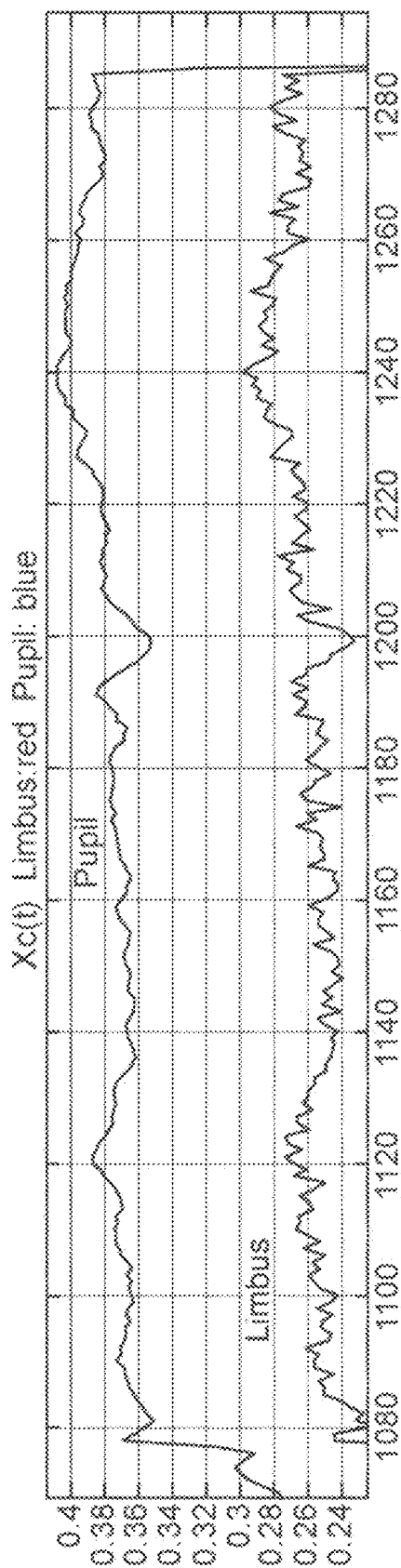
FIGS. 3A-3E are graphical more specific flow charts illustrating, in a non-limiting manner, a possible method for eye tracking according to some embodiments of the present invention.
Figure 3B:
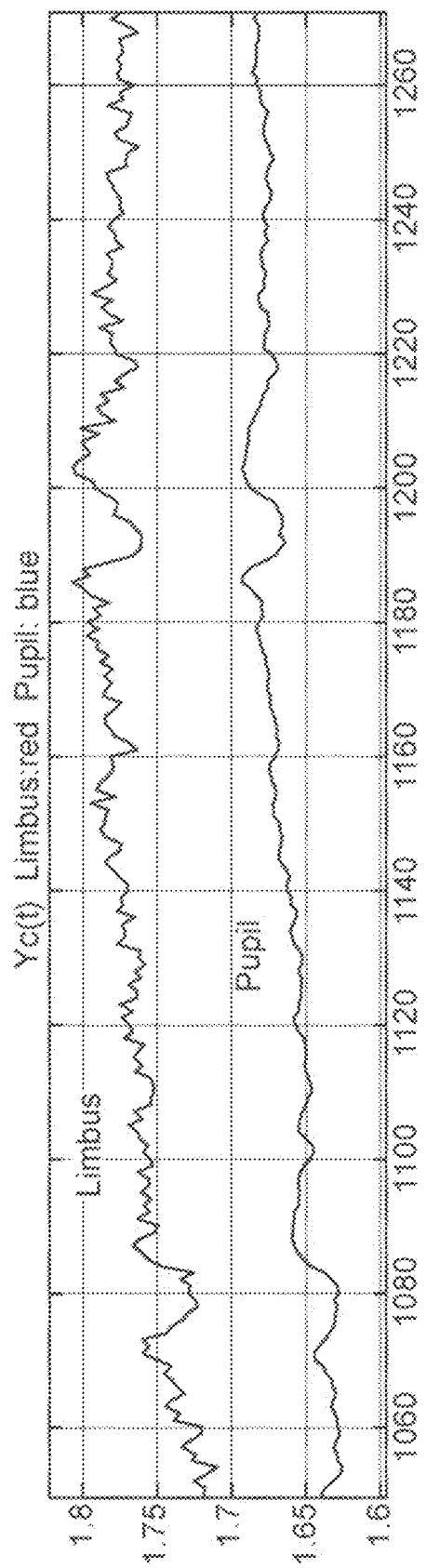
Figure 3C:
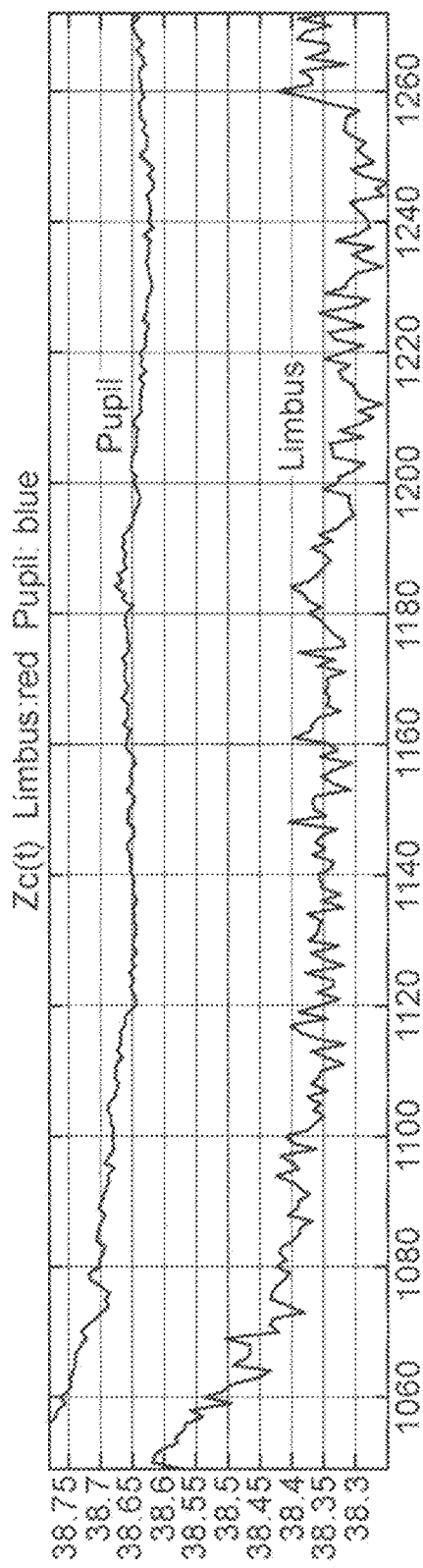
Figure 3D:
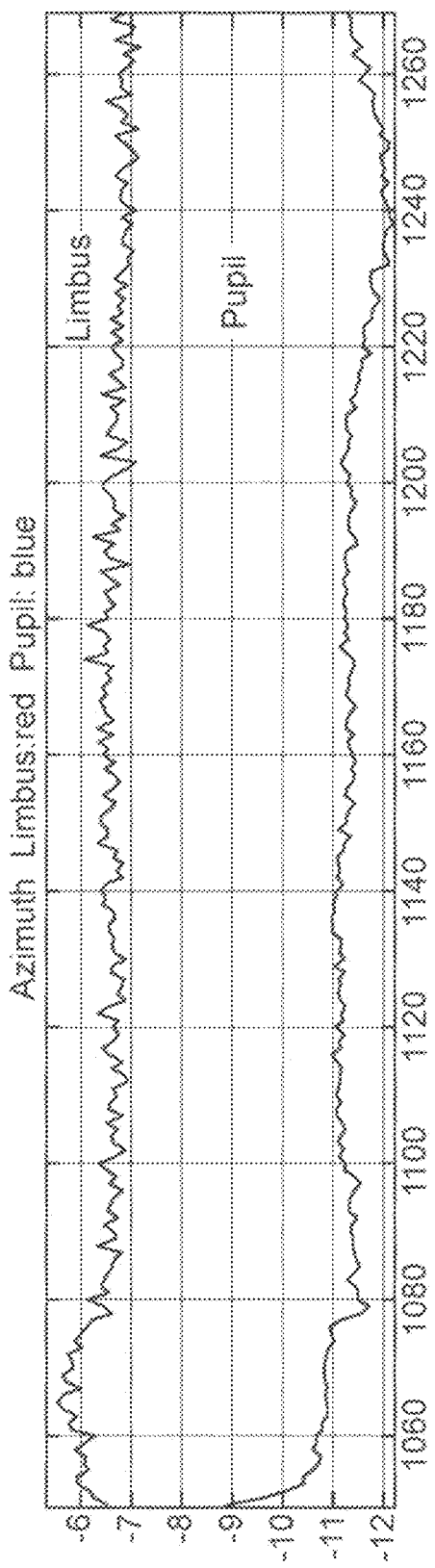
Figure 3E:
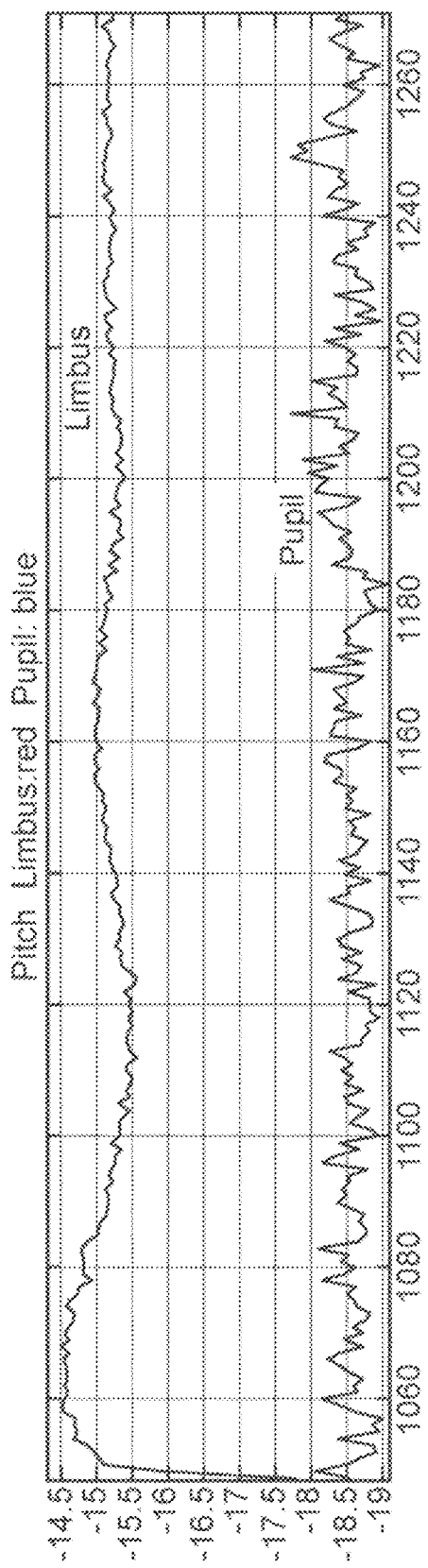

In some embodiments, method 200 may comprise capturing in 210 at least one image of a user's eye. This may be implemented by using any suitable image sensor. Reference is made to FIGS. 3A-3E, showing an example of a possible correlation between the limbus parameters and the pupil parameters. FIG. 3A shows the pupil data (first data) correlated with the limbus data (second data) for the X coordinate as a function of time. As clearly shown in the figure, the pupil data is more precise (less noisy) than the limbus data. FIG. 3B shows the pupil data (first data) correlated with the limbus data (second data) for the Y coordinate as a function of time. FIG. 3C shows the pupil data (first data) correlated with the limbus data (second data) for the Z coordinate as a function of time. FIG. 3D shows the pupil data (first data) correlated with the limbus data (second data) for the azimuth coordinate as a function of time. FIG. 3E shows the pupil data (first data) correlated with the limbus data (second data) for the pitch coordinate as a function of time.

Figure 4A:
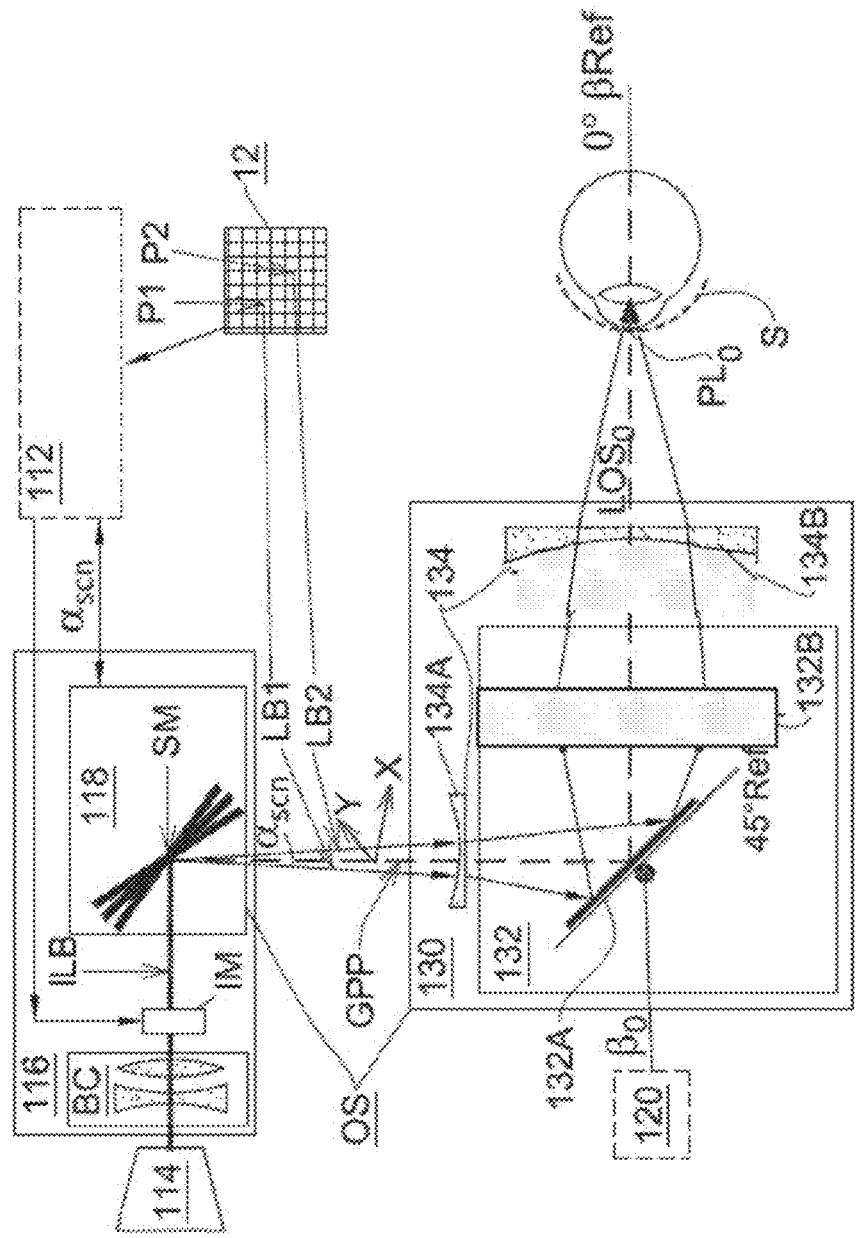
FIGS. 4A and 4B exemplify an eye projection system of the present invention having an eye projection optical module including a gaze tracking deflector comprising a field selector optical module utilizing a diffractive structure.
Figure 4B:
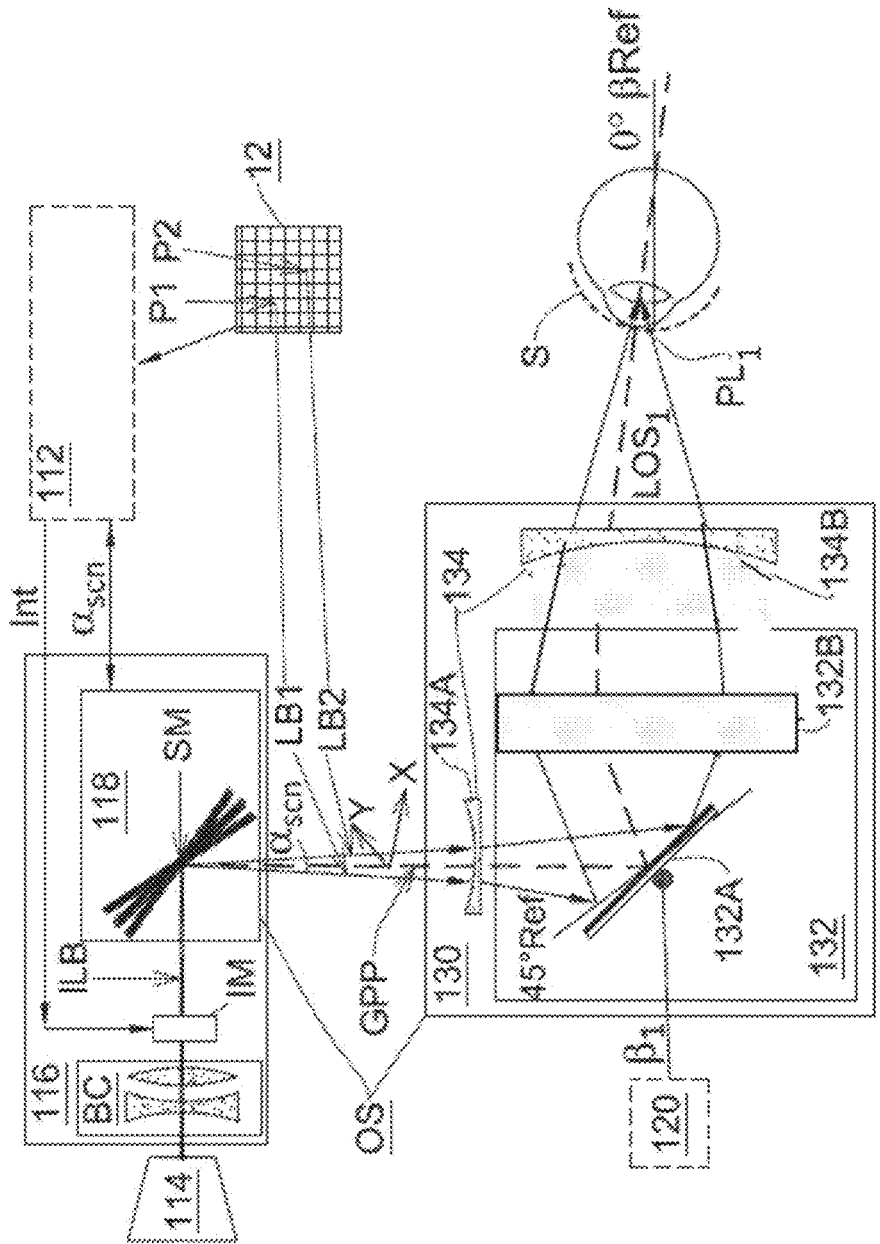

Reference is made to FIGS. 4A and 4B schematically illustrating an eye projection optics 130 of the present invention. Particularly shown in these figures, is an example of the system operation in two different gaze directions $\beta_0$ and $\beta_1$ of the eye.

The eye projection optics 130 includes a gaze tracking deflector module 132 and an angular beam relay module 134. The gaze tracking deflector module 132 is adapted for deflecting a general light propagation path GPP of a light beam towards the eye, in accordance with the gaze direction $\beta$ of the eye (i.e., in accordance with the direction of the eye's line of sight direction of the eye and the pupil's location in different gaze directions).

The angular beam relay module 134 is an optical system configured to relay the light beam outputted from an image scanner 118 with output projection angle $\alpha_{scn}$ and direct it to be incident onto a pupil EP of a user's eye with appropriate pupil incidence angle $\alpha_{in}$. In this example, the image scanner 118 includes one or more scanning mirrors SM, which perform scanning/raster-scanning of the light beam (e.g., by rotating the mirrors), during which the light beam is deflected to propagate over a range of image projection angles $\alpha_{scn}$ (measured with respect to the general light propagation path GPP), where typically each projection angle corresponds to a pixel of image 12 projected on the retina. The scanning/raster-scanning mirror(s)/deflectors may be implemented utilizing any suitable technique, for example electro optical deflectors and/or using mirrors. such as Micro Electro Mechanical System (MEMS) mirrors mechanically coupled to suitable actuators, such as Piezo-electrical actuators or other types of actuators, enabling the mirrors to deflect a light beam from light module 114 to perform an image/raster scan of the light beam across a range of projection angles $\alpha_{scn}$.

An image projection angle $\alpha_{scn}$ may be of a two dimensional value $\{\alpha^X_{scn}\ \alpha^Y_{scn}\}$ corresponding to the horizontal and vertical image projection angles. For example, the angles $\{\alpha^X_{scn}\ \alpha^Y_{scn}\}$ may respectively correspond to the angles between the general light propagation path GPP and the light beam's projections on two planes spanned by the general light propagation path GPP and two lateral axes X and Y orthogonal to the light propagation path GPP. In FIGS. 4A and 4B, for clarity only, a single scanning mirror SM (e.g., fast scanning mirror) is illustrated (e.g., being gimbaled for rotation in two dimensions/axes), while generally two or more mirrors/deflectors may be used to deflect the light beam in the two dimensional image projection angles $\alpha_{scn}$ (i.e., $\{\alpha^X_{scn}\ \alpha^Y_{scn}\}$).

Two light beam portions LB1 and LB2 are illustrated in the figures being deflected from the image scanner in two different image projection angles $\alpha_{scn1}$ and $\alpha_{scn2}$, which propagate through the eye projection optics 130. The angular beam relay module 134 includes two or more optical modules 134A and 134B, which are arranged along an optical path from the image scanner to the eye and configured to direct the light beam to be projected on the pupil with pupil incident angles $\alpha_{in}$ (here $\alpha_{in1}$ and $\alpha_{in2}$ of beams LB1 and LB2 respectively) corresponding to the image projection angles $\alpha_{scn}$ ($\alpha_{scn1}$ and $\alpha_{scn2}$). This is implemented by utilizing first and second optical modules 134A and 134B having optical powers (respectively associated with first and second focal lengths), and arranging the first and second optical modules 134A and 134B such that they are spaced apart from one another along the optical path of the light LB1 and LB2 propagating from the image scanner to the pupil by an optical distance that substantially equals a sum of said first and second focal lengths. To this end the angular beam relay 134 provides monotonic functional correspondence between the image projection angles $\alpha_{scn}$ at which the light beam portions (e.g., LB1 and LB2) are deflected from the image scanner, and the angles of pupil incidence $\alpha_{scn}$ at which they impinge on the pupil. This provides for the directed imaging on the retina of the eye.

It should be noted that the same or similar functional operation of the angular beam relay module 134 may be achieved by utilizing/including additional optical modules in the angular beam relay 134, which may have different relations between their optical powers (focal lengths) and their arrangement in the optical path. It should also be noted that the optical modules (e.g., 134A and 134B) of the angular beam relay 134 may include one or more optical elements which may also be functional elements integrated with other optical elements of the system 100.

The gaze tracking deflector module 132 is connectable to the gaze tracking controller 120 for receiving therefrom signals/data indicative of the gaze direction of the eye 13. The gaze tracking deflector module 132 is configured and operable for deflecting an optical propagation path of the light beam LB in accordance with signals/data (e.g., operating signals) from the gaze tracking controller 120, for changing/adjusting an optical function of the eye projection optics 130 in accordance with the gaze direction β of the eye. The gaze tracking controller 120 may be configured and operable for controlling the gaze tracking deflector 132 state (deflection operation/direction) so as to fully or at least partially compensate for a shift in the gaze direction β of the eye from the nominal gaze direction (indicated in the figures by 0° β-Ref). In the latter case, additional and complementary compensation may be provided by the image scanning function.

The configuration and operation of such eye projection optics 130 and the gaze tracking controller are described in U.S. Pat. No. 10,539,789, assigned to the assignee of the present application.

FIGS. 4A and 4B show schematic illustrations of the optical path of two light beams LB1 and LB2, corresponding to two different pixels of the image 12, and in particular show the operation of the gaze tracking deflector module 132 in two different gaze states/directions $\beta_0$ and $\beta_1$ of the eye respectively. As illustrated, in the different gaze states $\beta_0$ and $\beta_1$ the pupil is located in, respectively, two different pupil locations $PL_0$ and $PL_1$ on a virtual surface S (being a portion of a substantially spherical virtual surface) defining the possible locations of the pupil when eye gazes at different directions, and two different line of sight $LOS_0$ and $LOS_1$ of the eye in the different gaze directions. The gaze tracking deflector module 132 includes optical elements/modules adapted for compensating for both the shift in the pupil's location and the shift in line of sight of the eye associated with different gaze directions.

For example, the gaze tracking deflector module 132 includes: an adjustable/addressable optical deflector 132A (e.g., being an addressable gaze tracking mirror) and a field selector optical module 132B which are configured and operable together for controlling the propagation of light beams LB (e.g., LB1 and LB2 in the figures) of different image pixels to intersect with the respective locations of the pupil ($LP_0$, and $LP_1$ in the figures) when it gazes in different directions, and also to adjust the pupil incidence angles $\alpha_{in}$ of the light beam LB on the pupil (here $\alpha_{in1}$ and $\alpha_{in2}$ of beams LB1 and LB2 respectively) with respect to the lines of sight LOS (here $LOS_0$ and $LOS_1$ correspond to two different gaze directions) such that the incidence angles $\alpha_{in}$ remain fixed with respect to the line of sight LOS of the eye and are invariant to changes in the line of sight LOS direction of the eye/pupil.

The adjustable/addressable optical deflector 132A is addressable in the sense that it is responsive to input signals indicative of the gaze direction (or signals indicating the address/orientation angle of the deflector 132A corresponding to the gaze direction β) and is operable/shiftable for adjusting its orientation angle/deflection angle respectively so as to deflect the light beam LB to propagate along a respective optical path corresponding to the gaze direction β.

The field selector optical module 132B includes one or more light directing optical elements (i.e. element(s) applying optical power to a light beam interacting therewith), and is therefore configured and operable to receive beams LB of light propagating along various respective optical paths corresponding to different gaze directions and direct them to the corresponding location of the pupil at the respective gaze directions, to incidence on the pupil with the appropriate incidence angles.

The adjustable/addressable optical deflector 132A is located in between the first and second optical modules 134A and 134B of the angular beam relay module, along the general light propagation optical path GPP of path of the light beams LB (e.g., LB1 and LB2) from the image scanner 118. The field selector optical module 132B of the gaze tracking deflector module 132 may be located along the optical path GPP downstream from the adjustable/addressable optical deflector 132A with respect to the light propagation direction.

The field selector optical module 132B may be located before or after the second optical module 134B of the angular beam relay 134, and/or it may be integrated therewith to form an integral optical component performing the functions of both the field selector 132B and the second optical module 134B of the angular beam relay 134.

The field selector optical module 132B is configured as a diffractive structure including one or more diffractive elements. Such diffractive structure receives the light beams from the gaze tracking addressable optical deflector 132A and directs them to the pupil. The field selector may be implemented as a reflective/semi-reflective-beam-splitting surface/coating. For example, it may include an off-axis parabolic deflector.

The field selector optical module 132B configured as a diffractive structure having optical power, may be implemented as a diffraction grating adapted to create any desired diffraction pattern (periodic or not). The pattern diffracts the input beam coming from different directions into a reproduction of the received input beams.

More specifically, the diffractive element is configured and operable to receive beams of light propagating from the gaze tracking deflector along various respective optical paths corresponding to different gaze directions and direct them towards corresponding spatial locations at which the pupil is located when at these different gaze directions respectively. Therefore, the diffractive element is configured for changing the direction of the received input beams of light to directions corresponding to spatial locations of the pupil.

Using the diffractive structure in the field selector optical module makes the entire module smaller and lighter in weight. Also, when using the eye projection system with eyeglasses, the use of the diffractive structure advantageously allows to provide the right optical angles, even sharp ones, while keeping the glass surfaces at angles relative to the eye which are typical to normal glasses.

The invention claimed is:

1. An eye tracking device, comprising:
a processing unit configured and operable for:
receiving at least one image being indicative of a user's eye;
identifying in the image a first data being indicative of pupil's parameters;
receiving a second data being indicative of an alternative eye tracking, wherein the second data is more accurate than the first data; and
correlating between the first and second data and determining a three-dimensional position and gaze direction of the user's eye.

2. The eye tracking device of claim 1, wherein said processing unit is configured and operable to receive a second data comprising at least one of eye position, gaze direction, parameters of the eye, parts of eye location, rotation of the eye around optical axis, or eyelid's location.

3. The eye tracking device of claim 2, wherein said processing unit is configured and operable to receive the parameters of the eye comprising at least one limbus tracking parameter including at least one of limbus center X, Y and Z, limbus plane pitch or limbus plain yaw.

4. The eye tracking device of claim 3, wherein said processing unit is configured and operable to construct a regression map between the pupil tracking and the at least one limbus tracking parameter.

5. The eye tracking device of claim 4, wherein said processing unit is configured and operable to receive at least one limbus tracking parameter and to update the regression map accordingly.

6. The eye tracking device of claim 1, wherein said processing unit is configured and operable to identify in the image a first data comprising a pupil position and at least one of a pupil orientation, diameter or shape of the pupil.

7. The eye tracking device of claim 1, wherein said processing unit is configured and operable to correlate between the first and second data by applying a regression model.

8. The eye tracking device of claim 7, wherein said processing unit is configured and operable to construct a regression map between the pupil tracking and the alternative eye tracking parameters.

9. The eye tracking device of claim 8, wherein said processing unit is configured and operable to receive the alternative eye tracking parameters and to update the regression map accordingly.

10. The eye tracking device of claim 7, wherein said processing unit is configured and operable to determine a three-dimensional position and gaze direction of the user's eye by extrapolation the first data using the regression model.

11. The eye tracking device of claim 1, wherein said processing unit is configured and operable to perform a data fusion between the first and second data.

12. A method for eye tracking, the method comprising:
receiving image data indicative of at least one image of a user's eye;
identifying in the image a first data being indicative of pupil's parameters;
receiving a second data being indicative of alternative eye tracking, wherein the second data is more accurate than the first data; and
correlating between the first and second data to thereby determine a three-dimensional position and gaze direction of the user's eye.

13. The method of claim 12, further comprising capturing at least one image of a user's eye.

14. The method of claim 12, wherein receiving a second data comprises receiving at least one of eye position, gaze direction, parameters of the eye, parts of an eye location, rotation of the eye around optical axis, or eyelid's location.

15. The method of claim 14, wherein receiving said parameters of the eye comprise receiving at least one limbus tracking parameter including at least one of limbus center X, Y and Z, limbus plane pitch or limbus plain yaw.

16. The method of claim 15, further comprising constructing the regression map between the pupil tracking and the at least one limbus tracking parameter.

17. The method of claim 16, further comprising receiving at least one limbus tracking parameter and updating the regression map accordingly.

18. The method of claim 12, wherein identifying in the image a first data comprises identifying a pupil position and at least one of a pupil orientation, diameter and shape of the pupil.

19. The method of claim 12, further comprising applying a regression model to correlate between the first and second data.

20. The method of claim 19, further comprising constructing a regression map between the pupil tracking and the alternative eye tracking parameters.

21. The method of claim 20, further comprising continuously receiving alternative eye tracking parameters and updating the regression map accordingly.

22. The method of claim 19, further comprising extrapolating the first data using the regression model to determine the three-dimensional position and gaze direction of the user's eye.

23. The method of claim 12, further comprising performing a data fusion between the first and second data.

* * * * *